United States Patent
Buess et al.

(10) Patent No.: US 6,248,060 B1
(45) Date of Patent: Jun. 19, 2001

(54) RIGID ENDOSCOPE WITH SECOND ILLUMINATION SYSTEM LATERALLY OFFSET FROM FIRST ILLUMINATION SYSTEM

(75) Inventors: Gerhard Fritz Buess, Tuebingen; Ernst Flemming, Baierbrunn; Wolfgang Juergen Kunert; Marc Oliver Schurr, both of Tuebingen; Edward Naujoks; Johannes Tschepe, both of Berlin, all of (DE)

(73) Assignee: MGB Endoskopische Geraete GmbH Berlin, Berlin (DE)

( * ) Notice: Subject to any disclaimer, the term of this patent is extended or adjusted under 35 U.S.C. 154(b) by 0 days.

(21) Appl. No.: 09/242,259

(22) PCT Filed: Aug. 12, 1997

(86) PCT No.: PCT/DE97/01767

§ 371 Date: Feb. 12, 1999

§ 102(e) Date: Feb. 12, 1999

(87) PCT Pub. No.: WO98/06318

PCT Pub. Date: Feb. 19, 1998

(30) Foreign Application Priority Data

Aug. 12, 1996 (DE) .................................................. 19632445
Sep. 18, 1996 (DE) .................................................. 19637963

(51) Int. Cl.[7] .................................. A61B 1/07; A61B 1/12

(52) U.S. Cl. .......................... 600/182; 600/130; 600/169; 600/171; 600/177; 600/178

(58) Field of Search .................................. 600/104–107, 600/129, 130, 160, 169, 166, 111, 171, 177, 178, 180, 182; 433/29; 385/117

(56) References Cited

U.S. PATENT DOCUMENTS

| 3,903,877 | | 9/1975 | Terada . | |
|---|---|---|---|---|
| 4,072,147 | * | 2/1978 | Hett | 600/108 |
| 4,076,018 | | 2/1978 | Keckele . | |
| 4,272,156 | * | 6/1981 | Ishibashi et al. | 600/177 |

(List continued on next page.)

FOREIGN PATENT DOCUMENTS

| 1269287 | 8/1964 | (DE) . |
|---|---|---|
| 126304 | 7/1977 | (DE) . |
| 2942982C2 | 4/1980 | (DE) . |
| 3113869A1 | 1/1982 | (DE) . |
| 9405714 | 12/1994 | (DE) . |
| 0075415A2 | 3/1983 | (EP) . |
| 0369937A1 | 5/1990 | (EP) . |
| 067425A1 | 4/1995 | (EP) . |
| 0722107A2 | 7/1996 | (EP) . |
| 2011111A | 7/1979 | (GB) . |
| 2197496A | 5/1988 | (GB) . |

Primary Examiner—John P. Leubecker
(74) Attorney, Agent, or Firm—Venable; George H. Spencer; Robert Kinberg (57) ABSTRACT

A rigid endoscope includes a jacket tube with an optical system and, parallel to the optical axis of the optical system, a first glass fiber bundle which emits a beam to illuminate an object to be examined. A second optical illumination system is directed at the object being examined. The second light exit of the second optical illumination system is recessed from the first light exit of the optical system by a distance greater than a diameter of the jacket tube. The light exit axis at the second light exit of the second optical illumination system is offset laterally relative to the image axis at the distal end of the optical system by an amount such that because of the resultant parallax and the shadow formation and unequal light distribution thus attained, the vividness of the image impression for three dimensional objects is increased.

21 Claims, 4 Drawing Sheets

U.S. PATENT DOCUMENTS

| | | | |
|---|---|---|---|
| 4,697,577 | * 10/1987 | Forkner | 600/173 |
| 4,727,416 | 2/1988 | Cooper . | |
| 4,868,644 | * 9/1989 | Yabe et al. | 600/107 |
| 5,101,468 | 3/1992 | Chiu . | |
| 5,159,380 | * 10/1992 | Furuya et al. | 600/180 |
| 5,207,213 | 5/1993 | Auhll et al. . | |
| 5,456,245 | 10/1995 | Bornhop et al. . | |
| 5,533,496 | 7/1996 | De Faria-Correa . | |
| 5,605,532 | * 2/1997 | Schermerhorn | 600/169 |
| 5,730,700 | * 3/1998 | Walther et al. | 600/108 |
| 5,730,702 | * 3/1998 | Tanaka et al. | 600/180 |
| 5,940,126 | * 8/1999 | Kimura | 600/111 |

* cited by examiner

RIGID ENDOSCOPE WITH SECOND ILLUMINATION SYSTEM LATERALLY OFFSET FROM FIRST ILLUMINATION SYSTEM

BACKGROUND OF THE INVENTION

The present invention relates to a rigid endoscope, comprising a jacket tube having an optical system and a first glass fiber bundle shining parallel to the image axis of the optical system, for illuminating an object to be examined, and a second optical illumination system also aimed at the object to be examined.

It is known in principle that a rigid optical system for endoscopy, hereinafter called a rigid endoscope, comprises an optical system used for imaging a light source for illuminating the object being examined. It is also known, for instance from European Patent No. 0 369 937 A1, that the light source is realized with a glass fiber bundle, or so-called optical wave guide, located parallel to the optical axis of the optical system. In the prior are, the light from an external light source is input into the glass fiber bundle at the proximal end (the side toward the user) via a further glass fiber bundle, the so-called optical fiber cable. Via the glass fiber bundle, the light is transmitted to the distal end of the endoscope (the side toward the object being examined). The light source thus shines from the direction of the observer onto the object.

However, such endoscopes have the disadvantage that surgical instruments located in front of the optical system of the endoscope during the operation generally cast no shadow on the organs being examined. This is because articles introduced between the observer and the object being observed, hereinafter called the image background, are known not to cast shadows on the image background, if the light exit axis of the light source and the optical image axis of the observer coincide. Because of the endoscopic two-dimensional image, the surgeon already lacks depth information about the three-dimensional space being examined, and thus the three-dimensional impression of the region of the operation is restricted. In the endoscopes mentioned, this three-dimensional impression is restricted still further by the unnatural lighting or the absence of the shadow.

In angled endoscopes, such as a laparoscope with a 30° viewing direction, there is a slight asymmetry, because of constructional requirements, between the light exit axis of the light source and the optical image axis of the observer. However, this asymmetry is kept as slight as possible, so that the angle between the light exit axis of the light source and the optical image axis of the observer tends toward zero, and shadow formation, which would increase the plasticity of image reproduction, is negligibly slight.

From German Patent 29 42 982 C2, an endoscope is known in which two light sources are provided for illuminating the near and far region in front of the optical system of the endoscope. Both light sources are embodied in the form of optical wave guides, whose free ends crosswise to the longitudinal direction of the endoscope are disposed immediately next to the distal end of the optical system of the endoscope. The light exits of the first light source extends parallel to the image axis of the optical system of the endoscope and thus to the viewing direction of the observer. To exclude the influence of parallax in the illumination of the near region by the first light source, the light exit axis of the second light source is inclined relative to the image axis of the optical system of the endoscope; the light exit axis of the second light source and the image axis of the optical system of the endoscope intersect, in the viewing direction of the user, in front of the optical system of the endoscope. The far region in front of the optical system of the endoscope is illuminated by the first light source that shines parallel to the image axis of the optical system of the endoscope, and the near region in front of the optical system of the endoscope is illuminated by the second light source, which shines in inclined fashion relative to the image axis of the optical system of the endoscope. However, like the endoscopes already discussed above, this endoscope, because of the only slight spacing between the distal end of the optical system of the endoscope and the free ends of the first and second optical wave guides, has negligibly slight shadow formation.

SUMMARY OF THE INVENTION

It is therefore the object of the invention to furnish an endoscope in which the vividness of image impression, for three-dimensional objects, such as surgical instruments, observed through the optical system, is increased.

The invention encompasses the teaching that increasing the vividness of image impression with three-dimensional objects is attainable if the light exit direction at the light exit of the second optical illumination system is offset laterally, relative to the viewing direction at the distal end of the optical system, that is, along the image axis of the optical system, by an amount such that for points on a three-dimensional object being examined, a parallax that has a value other than zero results with respect to the light exit of the second optical illumination system and of the distal end of the optical system. Preferably, the optical illumination system is also a glass fiber bundle. Because of this parallax, the shadow cast onto the image background by the observed three-dimensional object because of the light exiting from the second optical illumination system and the projection of the observed onto the image background, which projection originates at the distal end of the optical system, do not coincide. The surgeon looking through the optical system consequently sees the shadow of the observed three-dimensional object on the image background, and as a result the vividness of image impression is increased in a simple way. This shadow formation makes three-dimensional orientation in the body cavity being endoscoped considerably easier for the physician.

A further advantage of the endoscope of the invention is that the light from the two glass fiber bundles is superimposed in the three-dimensional space being examined. With regard to the light exit from the first and the second glass fiber bundle, there is again a parallax other than zero, and because of this an uneven distribution of light in the space being observed is attained, which in turn makes the topographical contrast on the object being examined and in the image background greater, thus advantageously also making them appear more vivid to the surgeon. The space being observed is also illuminated more diffusely or uniformly.

The light exit from the second glass fiber bundle can be disposed at a suitable distance perpendicular to the longitudinal axis of the endoscope, next to the distal end of the optical system. Because the diameter of an endoscope should be kept slight, the resultant parallax and the attendant shadow formation are relatively limited however. The light exit of the second glass fiber bundle is therefore preferably recessed by a distance (d) from the distal end of the optical system. As a result, even with a slight endoscope diameter, a relatively great parallax and thus an especially vivid image impression are attainable. The distance (d) is preferably approximately 5 to 50 mm.

In advantageous embodiments of the invention, the glass fibers of the first and/or second glass fiber bundle are distributed over an angular region coaxially about the optical system. As a result, particularly if the second glass fiber bundle is recessed, shading of a considerable portion of the space being observed by the distal end of the optical system or of the jacket tube is avoided, and thus an especially favorable illumination of the space being observed is attained. Preferably, the glass fibers of the first and/or second glass fiber bundle has a crescent-shaped cross section, because this produces an especially homogeneous distribution of the light exiting from the respective glass fiber bundle.

In especially favorable refinements of the invention, the light exit direction of the second glass fiber bundle and/or the viewing direction of the optical system is oriented in inclined fashion to the image axis of the optical system, or to the longitudinal axis of the jacket tube. The inclination of the light exit direction of the second glass fiber bundle to the image axis of the optical system has the effect that the beams of light emerging from the second glass fiber bundle illuminate the field of view covered by the optical system substantially completely, thereby assuring suitable shadow formation over the field of view covered by the optical system.

The inclination of the viewing direction of the optical system, that is, of the optical image axis of the optical system, relative to the longitudinal axis of the endoscope causes an inclination of the entire field of view covered by the optical system. As a result, on the one hand it is attained in a simple manner that the suitably focused beams of light emerging from the second glass fiber bundle can illuminate the entire field of view covered by the optical system, without any shading of a substantial portion of the field of view by the portion of the endoscope extending between the light exit of the second glass fiber bundle and the distal end of the endoscope. Second, it is thus attained that the parallax of points in the observed space, with respect to the light exit of the second glass fiber bundle and the distal end of the optical system, has a value other than zero over wide portions of the field of view covered by the optical system, thereby casting a shadow that is visible to the surgeon.

Particularly good illumination and shadow formation in the field of view covered by the optical system is obtained in particular if the light exit direction of the second glass fiber bundle and the viewing direction of the optical system are oriented, inclined in the same direction, relative to the longitudinal axis of the jacket tube.

Preferably, the light exit direction of the second glass fiber bundle forms an angle a of greater than zero with the viewing direction of the optical system, so that the beams emerging from the second glass fiber bundle illuminate the field of view covered by the optical system.

In preferred embodiments of the endoscope according to the invention, the second glass fiber bundle is integrated with the jacket tube, thus in a simple way creating an endoscope that presents little impediment to the lighting devices.

The glass fibers of the second glass fiber bundle have a plane-ground end face oriented perpendicular to their longitudinal direction. However, they may also be ground at an angle $\beta$ to such an end face. As a result, the angle of inclination of the light exit direction to the longitudinal axis of the jacket tube, or its angle $\beta$ to the image axis of the optical system, can be adjusted in a simple way, without having to dispose the glass fibers themselves at a corresponding angle to the longitudinal axis of the jacket tube or to the image axis of the optical system.

In especially favorable refinements of the endoscope of the invention, the light exit of the second, in particular plane-ground glass fiber bundle is longitudinally displaceable relative to the jacket tube. As a result, the distance between the light exit of the second glass fiber bundle and the distal end of the optical system can be varied in a simple way, and as a result the parallax of the points in the observed space also varies with respect to these two reference points, and in turn this allows the shadow, visible to the observer, cast by objects located in the observed space to be adjusted.

In preferred refinements of the endoscope of the invention, the proximal ends of the first and second glass fiber bundles are joined together in an optical fiber cable connection. Preferably, the number of individual glass fibers in the first and second glass fiber bundles are adapted per bundle to the quantity of light to be transmitted.

In preferred embodiments of the endoscope of the invention, at least one insufflation channel and/or at least one flushing channel, and preferably both, are provided in the jacket tube. $CO_2$ gas, for instance, can be insufflated through the insufflation channel into the observation space, and an isotonic liquid can be passed into this space through the flushing channel. The insufflation channel or the flushing channel is preferably disposed between the second glass fiber bundle and the optical system, so that as a result, in a simple way, a lateral spacing is attained between the light exit direction at the light exit of the second glass fiber bundle with respect to the viewing direction at the distal end of the optical system, which spacing already by itself assures a parallax required for the desired shadowing effect.

Preferably, a means for beam shaping is mounted on the respective distal ends of the insufflation channel and/or flushing channel, so that with the aid of the gas stream and/or the liquid stream, the distal end of the endoscope, and in particular the image entrance face, can be cleaned. In surgery that uses high-energy therapy devices, for instance, such as high-frequency surgery or laser surgery, in which the distal end of the endoscopes and in particular the image entrance face of the optical system become soiled, it thus becomes possible to use the endoscope without annoying interruptions for cleaning the image entrance face of the optical system.

When there are temperature differences between an optical system and its surroundings, a deposit of moisture on the optical system occurs, depending on the degree of saturation or in other words on the relative humidity of the air. In the application of endoscopy in question here, the surroundings of the optical system comprise from 90 to 100% saturated $CO_2$ gas at body temperature, so that the distal image entrance face of the optical system, in accordance with the dew point curve and depending on its current temperature, becomes more or less severely fogged. In a logical extension of the concept of the invention, a heater is provided in the jacket tube, which preferably tempers the insufflation gas, flushing liquid and/or jacket tube, including at least one of the glass fiber bundles, to body temperature and thus prevents fogging of the distal image entrance face of the optical system. Alternatively, fogging of the distal image entrance face of the optical system is reduced by tempering the optical system and/or by means of the tempered gas stream aimed at the image entrance face.

BRIEF DESCRIPTION OF THE DRAWINGS

Other advantageous refinements of the invention are defined in the dependent claims and are described in further detail below along with the description of the preferred embodiment of the invention, in conjunction with the drawings. Shown are:

DETAILED DESCRIPTION OF THE INVENTION

Figure 1:
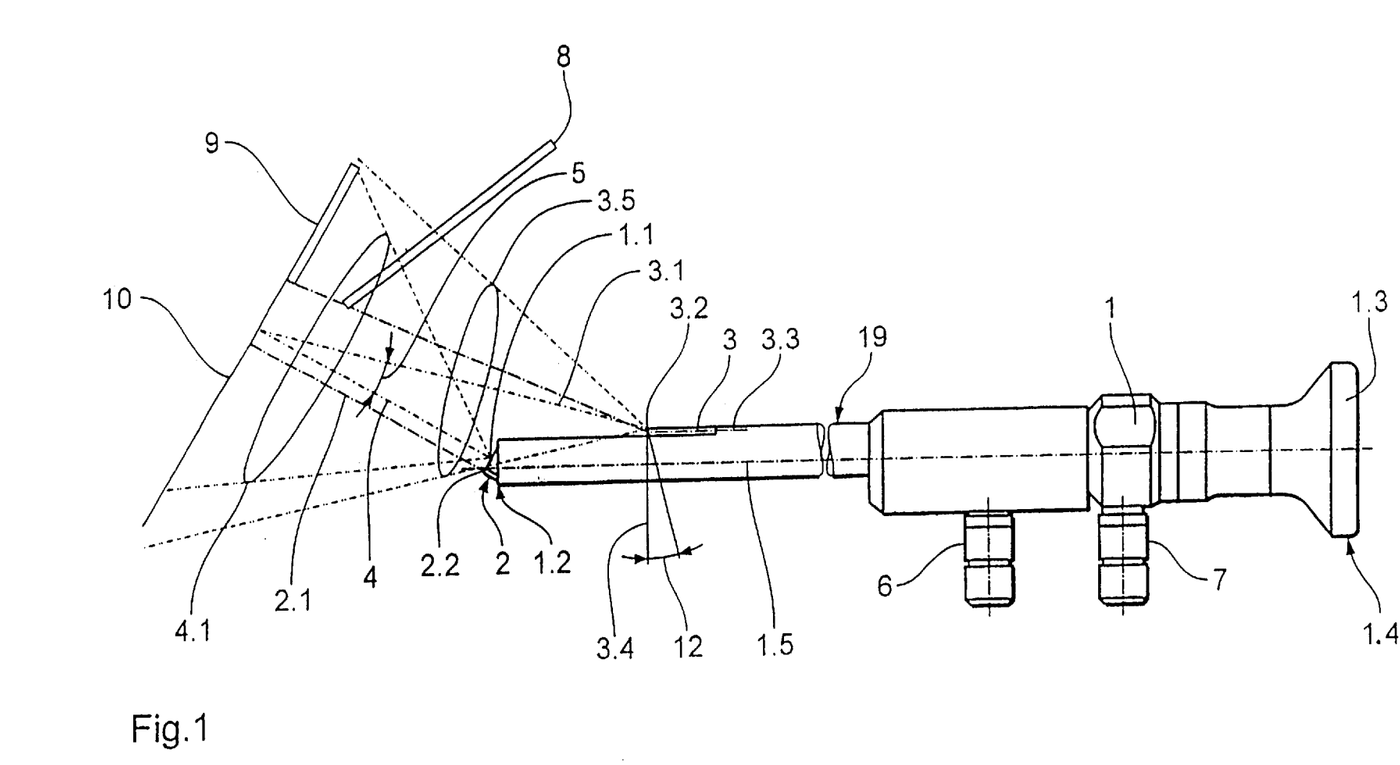
FIG. 1, a side view of a preferred exemplary embodiment of the invention.

FIG. 1 shows an elongated rigid endoscope with an optical system 1 integrated with a jacket tube 19, and with the first glass fiber bundle 2 and the second glass fiber bundle 3. The optical system 1 includes an objective 1.1, which is mounted on the distal end 1.2 of the endoscope, that is, on the end of the endoscope toward the object to be examined, and an ocular 1.3, which is located on the proximal end 1.4 of the endoscope, that is, on the end of the endoscope toward the surgeon. The objective 1.1 is disposed on the distal end 1.2 of the endoscope in such a way that the optical image axis 4 of the objective 1.1— and hence of the optical system 1—extends in inclined fashion to the longitudinal axis 1.5 of the endoscope by an angle of approximately 30°. The end face of objective 1.1 has a course component, perpendicular to the longitudinal axis 1.5, that points in the direction of the side of the endoscope on which the second glass fiber bundle 3 is disposed. The portion of the optical image axis 4 originating at the objective 1.1 and extending in the viewing direction of the surgeon is thus inclined, relative to the longitudinal axis 1.5 of the endoscope, by the aforementioned angle in the direction of the side of the endoscope on which the second glass fiber bundle 3 is disposed.

The light exit 2.2 on the distal end of the first glass fiber bundle 2 is also disposed on the distal end 1.2 of the endoscope, and the first glass fiber bundle 2 is oriented such that its light exit axis 2.1 extends parallel to the image axis 4 of the objective 1.1. The second glass fiber bundle 3 is recessed on the endoscope from its distal end 1.2, in the longitudinal direction of the endoscope. The distance (d) of the light exit 3.2 on the distal end of the glass fiber bundle 3 from the distal end 1.2 of the endoscope in the example shown is thus equivalent, in the longitudinal direction of the endoscope, to approximately three times the diameter of the endoscope on its distal end 1.2. Depending on the diameter of the endoscope, the distance (d) is between 5 and 50 mm. The light exit axis 3.1 of the second glass fiber bundle 3 is inclined by an angle 5 (that is, the angle α) from the image axis 4 of the objective 1.1; in the exemplary embodiment shown, this angle is approximately 15°. It is understood that the angle 5— depending on existing conditions—may also be selected differently.

To adjust the angle 5 of the light exit axis 3.1 of the second glass fiber bundle 3 relative to the image axis 4 of the objective 1.1, the glass fibers of the second glass fiber bundle 3 are beveled at the light exit 3.2. The end face of the glass fibers at the light exit 3.2 is inclined at an angle 12 (that is, the angle β) of approximately 13°—in the present exemplary embodiment, to the normal plane 3.4 on the longitudinal axis 3.3 of the second glass fiber bundle 3, with the end face toward the endoscope. As a result, the light exit axis 3.1 of the second glass fiber bundle 3 points away from the endoscope in the light exit direction. To attain the beveling on the distal end 3.2 of the second glass fiber bundle 3, the glass fibers are plane-ground accordingly. The angles 5 and 12 (that is, α and β) are in a direct relationship.

The second glass fiber bundle 3 is displaceable on the endoscope in the longitudinal direction of the endoscope. As a result, the distance between the light exit 3.2 of the second glass fiber bundle 3 and the distal end 1.2 of the endoscope and thus the distal end of the objective 1.1 can be varied. By a suitable choice of this distance, the shadow effect is adjusted for high contrast.

However, it is understood that in other advantageous embodiments of the invention the glass fibers of the second glass fiber bundle 3 are not ground at an angle 12 but rather can be embodied with an end face perpendicular to their longitudinal axis. The shadow effect can once again then be adjusted by means of the axial distance between the distal end 3.2 of the second glass fiber bundle 3 and the image axis 4.

The light for the glass fiber bundles 2 and 3 is input separately into the respective optical fiber cable connections 6 and 7. The light of the two glass fiber bundles 2 and 3 is superimposed in the observed space. An article 8 introduced into the observed space, because of the light exiting from the distal end 3.2 of the second glass fiber bundle 3, casts a shadow 9 on the image background 10. Because of the distance between the objective 1.1 mounted on the distal end 1.2 and the light exit 3.2 of the second glass fiber bundle 3, the shadow 9 and the projection of the article 8 onto the image background 10 originating at the distal end face of the objective 1.1 do not coincide. The surgeon looking through the ocular 1.3 consequently perceives the shadow of the article 8 on the image background 10.

The distance between the light exits 2.2 and 3.2 of the two glass fiber bundles 2 and 3, and their light exit directions 2.1 and 3.1 that are inclined relative to one another, also have the effect that the observed space is advantageously illuminated more diffusely or uniformly, and the topographical contrast both on the image background 10 and on the article 8 being examined is increased, so that the work of the surgeon is made substantially easier because of the increased vividness of image impression.

The inclination of the portion, originating in the viewing direction of the surgeon at the objective 1.1, of the optical image axis 4 relative to the longitudinal axis 1.5 of the endoscope in the direction of the second glass fiber bundle 3 brings about an inclination of the entire field of view 4.1 covered by the objective 1.1 relative to the longitudinal axis of the endoscope. As a result, on the one hand, it is attained in a simple manner that the cone of light 3.5, emerging from the second glass fiber bundle 3 and inclined in the same direction as the optical image axis 4 from the longitudinal axis 1.5, illuminates the entire field of view 4.1—except for a certain maximum distance of the endoscope from the image background 10—without the portion of the endoscope extending between the light exit 3.2 of the second glass fiber bundle 3 and the distal end 1.2 of the endoscope shading any substantial portion of the field of view 4.1. Second, it is thereby attained that the parallax of points on the article 8 relative to the light exit 3.2 of the second glass fiber bundle 3 and the distal end face of the objective 1.1 have a value other than zero over wide portions of the field of view 4.1, thus resulting in a shadow, visible to the surgeon, cast on the image background 10. Only in the small peripheral region of the field of view 4.1 in which the jacket lines of the conical boundary of the field of view 4.1 extend approximately parallel to the longitudinal axis of the endoscope does the shadow 9 disappear, with respect to the observer, more or less behind the article 8, because in this region the aforementioned parallax tends toward zero.

Figure 2:
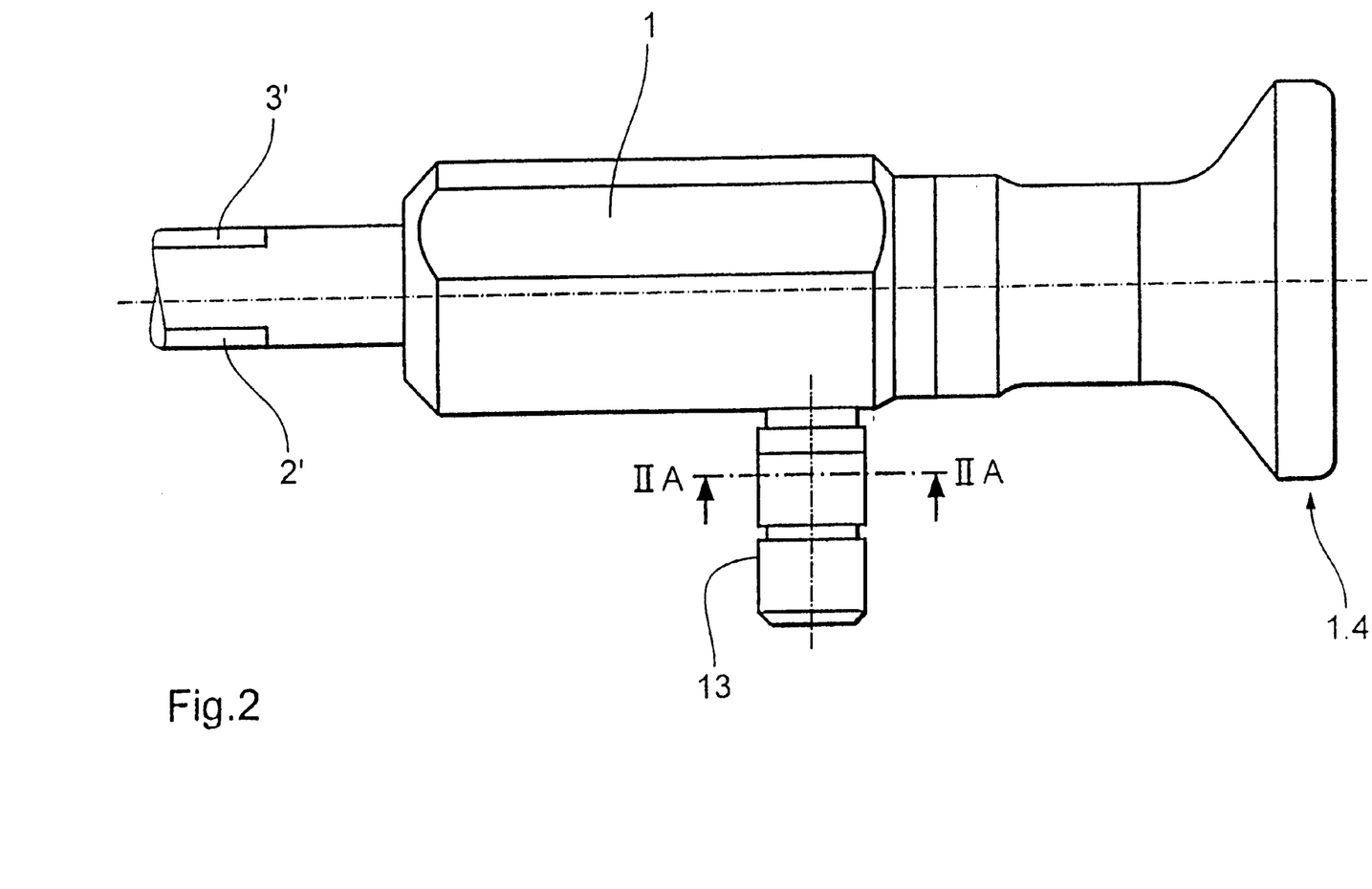
FIG. 2, side view of a further preferred exemplary embodiment of the invention.
Figure 2A:
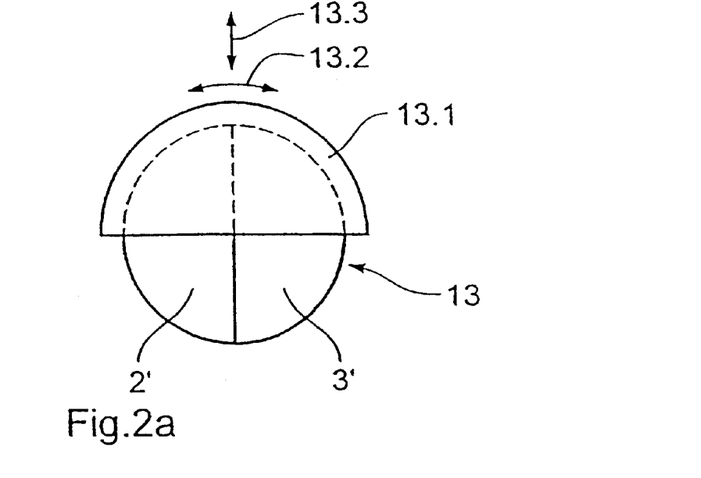
FIG. 2a, a schematic section through the optical fiber cable connection of FIG. 2.

In FIG. 2, the proximal end 1.4 of an endoscope is shown, which is substantially equivalent to the endoscope of FIG. 1. The difference from the endoscope of FIG. 1 is that the glass fiber bundles 2' and 3' are joined together in a common optical fiber cable connection 13. FIG. 2a shows a schematic sectional view of the optical fiber cable connection 13 taken along the line IIA—IIA of FIG. 2. The optical fiber cable connection 13 is provided with an aperture 13.1, which variably covers the cross section of the proximal ends of the two glass fiber bundles 2' and 3'. This aperture 13.1 can be displaced in its plane along the arrow 13.2, in order to cover the cross section of the proximal ends of the two glass fiber bundles 2' and 3' to a variable extent and thus adjust the quantity of light input into the proximal ends of the first and second glass fiber bundles 2' and 3'. To adjust the distribution of the total quantity of light input to the first and the second glass fiber bundle 2' and 3', the aperture 13.1 is rotatable in its plane along the arrow 13.3 about an axis perpendicular to the plane of the drawing. As a result, the ratio between the coverage of the cross section of the proximal end of the first glass fiber bundle 2' and the coverage of the cross section of the proximal end of the second glass fiber bundle 3' by the aperture 13.1, so that the distribution of the total quantity of light input through the optical fiber cable connection 13 to the two glass fiber bundles 2' and 3' can be adjusted. It is understood that such an adjusting device, in particular an aperture, and its adjustability can, however, be realized in manifold other known ways.

Figure 3:
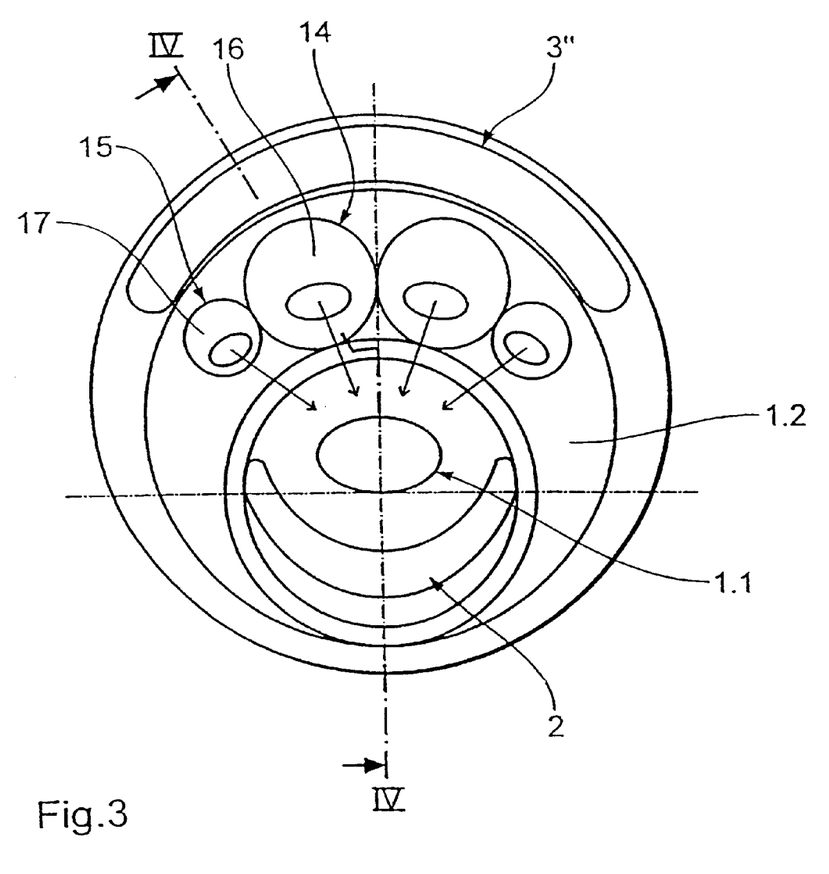
FIG. 3, a plan view on the distal end of an endoscope according to the invention.
Figure 4:
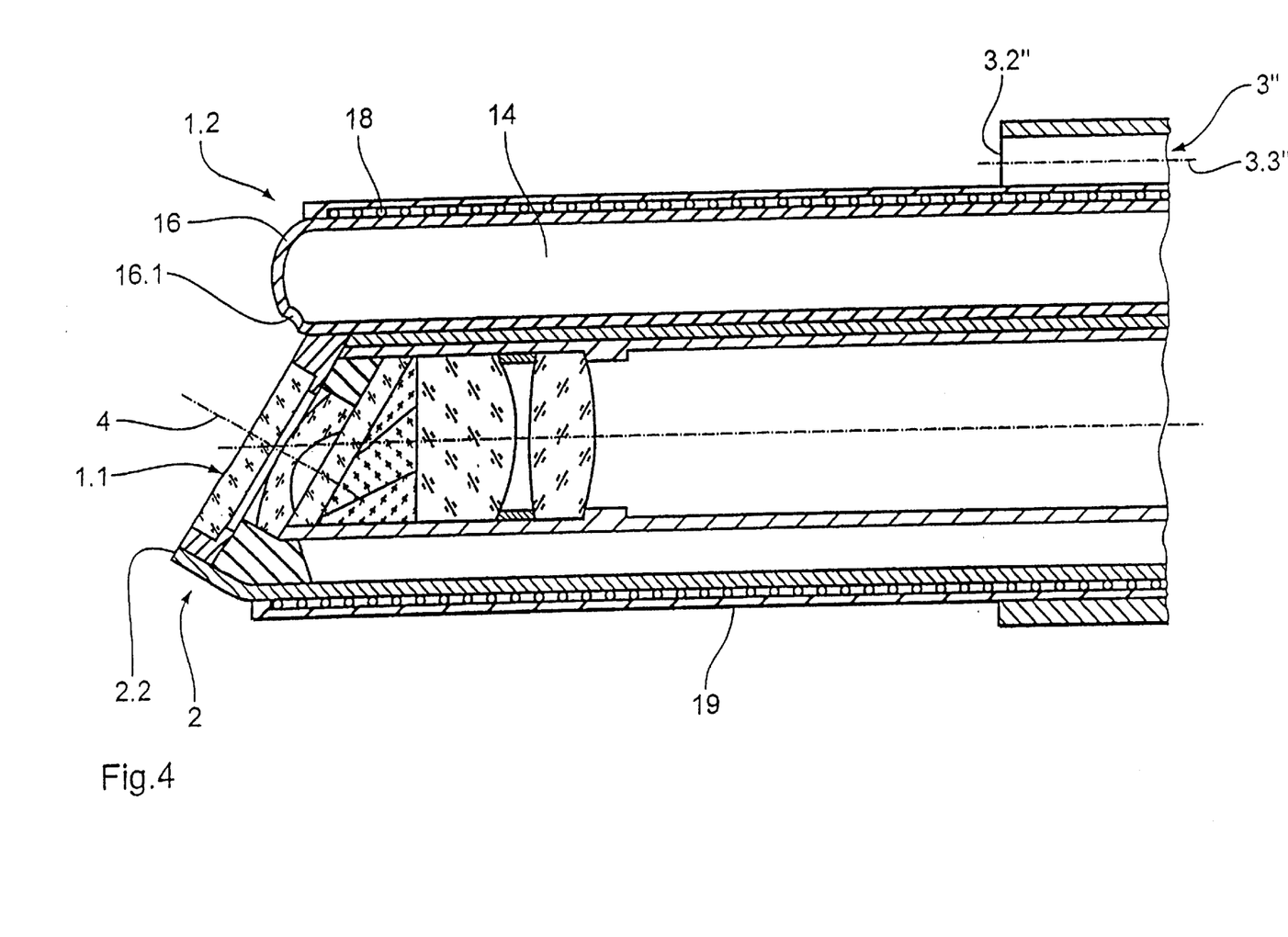
FIG. 4, a section through the distal end of the endoscope of FIG. 3, taken along the line IV—IV.

FIG. 3 shows a plan view on the distal end 1.2 of an endoscope that is substantially equivalent to the endoscope of FIG. 1; FIG. 4 shows a section through the distal end of the endoscope of FIG. 3 along the line IV—IV. The difference from the endoscope of FIG. 1 is that the end face on the distal end 3.2" of the second glass fiber bundle 3" is perpendicular to the longitudinal axis 3.3" of the second glass fiber bundle 3", and therefore the longitudinal axis 3.3" also forms the light exit axis of the second glass fiber bundle 3".

As can be seen from FIG. 3, the glass fibers of the first glass fiber bundle 2 are disposed coaxially around the optical system 1 over an angular range of approximately 180°, and the glass fibers of the second glass fiber bundle 3 are deposited coaxially about the optical system 1 over an angular range of approximately 120°. The first and second glass fiber bundles 2 and 3 have a crescent-shaped cross section.

Also in this embodiment of the invention, insufflation channels 14 and flushing channels 15 are integrated with the endoscope and are disposed between the second glass fiber bundle 3 and the optical system 1. $CO_2$ gas, for instance, can be insufflated through the insufflation channel 14, while isotonic flushing liquid is pumped through the flushing channel. The respective distal ends of the insufflation channels 14 and flushing channels 15 are closed off with beam-shaping means 16 and 17. As can be learned from FIG. 4, the means for beam shaping formed onto the insufflation channels 14 comprise an approximately hemispherical shell-like cap 16, which closes off the respective channel 14. This cap 16 is provided with an opening 16.1, which aims the insufflation gas stream at the objective 1.1. With the aid of the gas stream and the flushing liquid stream, the distal end 1.2 of the endoscope, and in particular the image entrance face of the objective 1.1, are cleaned. This prevents the distal end 1.2 of the endoscope, in particular the objective 1.1, from remaining uncleaned for long and making further work more difficult or even impossible in surgical operations that use high-energy therapy devices, such as high-frequency surgery or laser surgery.

If there are temperature differences between the optical system and its surroundings, a deposit of moisture on the optical system occurs, dependent on the degree of saturation, that is, the relative humidity of the air. In the application of endoscopy in question here, the surroundings of the optical system are 90 to 100% saturated $CO_2$ gas at body temperature, so that the distal image entrance face of the objective 1.1 becomes more or less markedly fogged in accordance with the dewpoint curve, depending on their current temperature. In a logical extension of the concept of the invention, a heater is therefore integrated with the endoscope in such a way that the insufflation gas, flushing liquid, and objective 1.1 are kept at body temperature, thus averting fogging of the objective 1.1, that is, the distal image entrance face of the optical system 1. In the example shown, the heater comprises an electric heating coil 18, which is embedded in the jacket tube 19 of the endoscope over the length of the endoscope and keeps the entire endoscope at body temperature.

The invention is not limited in its embodiment to the preferred exemplary embodiments described above. On the contrary, a number of variants are conceivable that make use of the realization described, even in fundamentally different kinds of embodiments.

What is claimed is:

1. A rigid endoscope, comprising a jacket tube having a distal end and enclosing an optical system, having an image axis and a first light exit at the distal end, and a first glass fiber bundle shining light exiting the first light exit parallel to the image axis of the optical system for illuminating an object to be examined, and a second optical illumination system, aimed at the object to be examined, having a second light exit and a light exit axis wherein the second light exit is recessed from the first light exit by a distance greater than a diameter of the jacket tube at the distal end of the endoscope and the light exit of the second optical illumination system is offset laterally relative to the image axis at the distal end of the optical system by an amount such that because of the resultant parallax and the shadow formation and unequal light distribution thus attained, the vividness of the image impression for three-dimensional objects is increased.

2. The endoscope of claim 1,
   wherein
      the second optical illumination system comprises a second glass fiber bundle.

3. The endoscope of claim 2,
   wherein
      the glass fibers of at least one of the first and second glass fiber bundle are distributed over an angular region coaxially about the optical system.

4. The endoscope of claim 3,
   wherein
      the glass fibers of at least one of the first and second glass fiber bundle have a crescent-shaped cross section.

5. The endoscope of claim 2,
wherein
the light exit axis of the second glass fiber bundle and the image axis of the optical system is oriented at an inclination to the longitudinal axis of the jacket tube.

6. The endoscope of claim 5,
wherein
the light exit axis of the second glass fiber bundle forms an angle $\alpha$ of greater than zero with the image axis of the optical system.

7. The endoscope of claim 2,
wherein
the second glass fiber bundle is integrated with the jacket tube.

8. The endoscope of claim 2,
wherein
both the light exits of the first and second glass fiber bundles and portion of the optical system toward the object are disposed in a region of the distal end of the endoscope.

9. The endoscope of claim 2, wherein the light exit axis of the second glass fiber bundle is inclined with respect to the image axis of the optical system.

10. The endoscope of claim 2, wherein the light exit axis of the second glass fiber bundle and the image axis of the optical system are both inclined in the same direction relative to the longitudinal axis of the jacket tube.

11. The endoscope of claim 2,
wherein
the glass fibers at the second light exit of the second glass fiber bundle present an end face that is one of (a) a ground plane and oriented perpendicular to the longitudinal direction and (b) ground so as to be inclined by an angle $\beta$ to a plane normal to the longitudinal direction of the second glass fiber bundle.

12. The endoscope of claim 11,
wherein
the light exit of the second glass fiber bundle is disposed longitudinally displaceably with respect to the jacket tube, in order to influence a shadow effect.

13. The endoscope of claim 2,
wherein
the first and second glass fiber bundles have proximal ends that are joined together in a common optical fiber cable connection.

14. The endoscope of claim 13,
wherein
the common optical fiber cable connection includes a device for adjusting at least one of a quantity of light input into the proximal ends of the first and second glass fiber bundles and a distribution of an input light quantity to the first and second glass fiber bundles.

15. The endoscope of claim 1,
wherein
the number of individual glass fibers in the first and second glass fiber bundles are adapted per bundle to a quantity of light to be transmitted.

16. The endoscope of claim 1,
further comprising at least one of (a)
at least one insufflation channel and (b) at least one flushing channel disposed in the jacket tube.

17. The endoscope of claim 16,
wherein the at least one of
the insufflation channel and the flushing channel is disposed between the second glass fiber bundle and the optical system (1).

18. The endoscope of claim 16,
further comprising
a means for beam shaping mounted on the respective distal ends of the at least one insufflation channel and flushing channel, so that with the aid of a gas stream in the insufflation channel and a liquid stream in the flushing channel, the distal end of the endoscope can be cleaned.

19. The endoscope of claim 18,
further comprising a means for heating
disposed in the jacket tube.

20. The endoscope of claim 19,
wherein the heating means is for at least one of (a) heating
at least one of the insufflation gas, flushing liquid, and jacket tube, including at least one of the glass fiber bundles, to body temperature and (b) tempering the gas stream aimed at the image entrance face for reducing fogging of the distal image entrance face of the optical system.

21. A rigid endoscope, comprising a jacket tube having a distal end and enclosing an optical system, having an image axis and a first light exit at the distal end, and a first glass fiber bundle shining light exiting the first light exit parallel to the image axis of the optical system for illuminating an object to be examined, and a second optical illumination system, aimed at the object to be examined, and comprising a second glass fiber bundle, and having a second light exit and a light exit axis, the light exit axis at the second light exit of the second optical illumination system being offset laterally relative to the image axis at the distal end of the optical system by an amount such that because of the resultant parallax and the shadow formation and unequal light distribution thus attained, the vividness of the image impression for three dimensional objects is increased, and further wherein the light exit of the second glass fiber bundle is disposed longitudinally displaceably with respect to the jacket tube in order to influence a shadow effect.

* * * * *